United States Patent [19]

Roger et al.

[11] Patent Number: 4,585,769
[45] Date of Patent: Apr. 29, 1986

[54] BENZENESULFONYL-LACTAMS AND THEIR USE AS ACTIVE SUBSTANCES OF PHARMACEUTICAL COMPOSITIONS

[75] Inventors: Pierre Roger, Montigny-les-Bretonneux; Patrick Choay, Paris; Jean-Paul Fournier, Versailles, all of France

[73] Assignee: DROPIC - Societe Civile de gestion de droits de propriete Industrielle CHOAY, Paris, France

[21] Appl. No.: 662,187

[22] Filed: Oct. 18, 1984

[30] Foreign Application Priority Data

Oct. 18, 1983 [FR] France .................... 83 16554

[51] Int. Cl.$^4$ .................... A61K 31/55; C07D 223/10; C07D 209/32; C07D 211/40
[52] U.S. Cl. .................... 514/212; 514/350; 514/423; 260/239.3 R; 546/216; 546/219; 548/542
[58] Field of Search .............. 260/239.3 R; 546/216, 546/219; 548/542; 514/212, 350, 423

[56] References Cited

PUBLICATIONS

Heldt, "J. Am. Chem. Soc.", vol. 80, pp. 5880–5885, (1958).

Primary Examiner—Robert T. Bond
Attorney, Agent, or Firm—Weiser & Stapler

[57] ABSTRACT

The invention relates to new benzenesulfonyl-lactams, process for their preparation and their use as active substance in pharmaceutical compositions.

Compounds according to the invention correspond to the general formula (I):

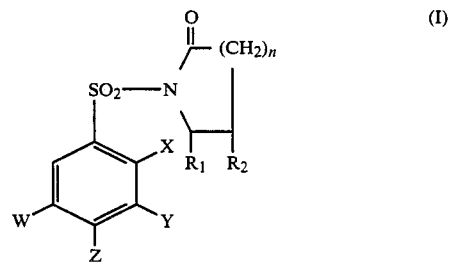

in which:
X can represent hydrogen,
Y can represent the $CF_3$ group,
Z can represent chlorine,
W can represent hydrogen,
n is 1, 2 or 3,
$R_1$ can represent hydrogen,
$R_2$ can represent the OH group, provided that when n is 2 or 3, X or Z represents an alkoxy group from 1 to 4 carbon atoms or that Y represents the $CF_3$ or $NO_2$ group, and when n is 1, Y or W represents the $CF_3$ group.

These new compounds may be introduced as active substances, particularly in the treatment of disorders of the memory.

19 Claims, No Drawings

BENZENESULFONYL-LACTAMS AND THEIR USE AS ACTIVE SUBSTANCES OF PHARMACEUTICAL COMPOSITIONS

The invention relates to new medicaments which present an activity upon the central nervous system, particularly psychotrope, with modifications of the behaviour and which contain, as active substance, chemical compounds the basic structure of which is of the benzenesulfonyl-lactam type, as well as their salts obtained with physiologically acceptable acids.

In the text, the term "medicament" designates any pharmaceutical composition, which contains one at least of the chemical compounds hereafter defined, in association with a pharmaceutically acceptable carrier.

The invention also relates to new compounds which constitute the active substance of the new compounds.

The invention also relates to a process for preparing the above said chemical compounds.

Benzenesulfonyl-lactams of formula:

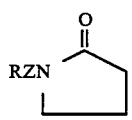

in which R represents $(R^2)_n C_6 H_{5-n} (CH_2)_m$—, $R^2$ representing H, an alkyl radical, an alkoxy radical, a halogen atom or a nitro group, n is varying from 1 to 5, m has the value of 0 or 1, Z can represent $SO_2$, are mentioned in the Chemical Abstracts, vol. 94, No. 156735v, 1981, p. 642.

The compounds are presented as quality improvers for citrus fruits.

The new medicaments according to the invention are characterized by the fact that they contain, as active substance, at least one of the compounds corresponding to the following general formula (I):

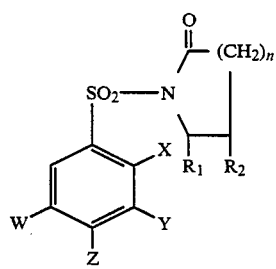

in which:
X represents a hydrogen atom, an alkoxy group from 1 to 4 carbon atoms;
Y represents a hydrogen atom, a $CF_3$ or $NO_2$ group;
Z represents a hydrogen atom, halogen, an alkoxy group from 1 to 4 carbon atoms, a $NO_2$ group;
W represents a hydrogen atom, halogen, a $CF_3$ group, a $NO_2$ group, an alkoxy group from 1 to 4 carbon atoms; n is 1, 2 or 3;
$R_1$ represents a hydrogen atom, an alkyl group from 1 to 6 carbon atoms;
$R_2$ represents a hydrogen atom, an OH group, an OR group in which R represents an alkyl group from 1 to 4 carbon atoms or an acyl group from 1 to 6 carbon atoms; provided that X or Z represents an alkoxy group from 1 to 4 carbon atoms or Y represents the $CF_3$ or $NO_2$ group.

This group will be designated by G1 in the following.

A preferred group of medicaments according to the invention is constituted by those the active substance of which is a compound of formula (I):

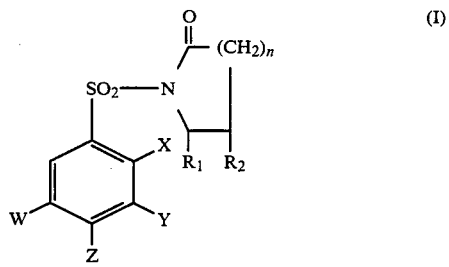

in which:
X represents a hydrogen atom, an alkoxy group from 1 to 4 carbon atoms;
Y represents a hydrogen atom, a $CF_3$ group, a $NO_2$ group;
Z represents a hydrogen atom, halogen, an alkoxy group from 1 to 4 carbon atoms, a $NO_2$ group;
W represents a hydrogen atom, halogen, a $CF_3$ group, a $NO_2$ group, an alkoxy group from 1 to 4 carbon atoms;
n is 1, 2 or 3;
$R_1$ represents a hydrogen atom, an alkyl group from 1 to 6 carbon atoms;
$R_2$ represents a hydrogen atom, an OH group, an OR group in which R represents an alkyl group from 1 to 4 carbon atoms or an acyl group from 1 to 6 carbon atoms; provided that when n is 1:
Y or W represents a $CF_3$ group; and when n is 2 or 3:
X or Z represents an alkoxy group from 1 to 4 carbon atoms or Y represents the $CF_3$ or $NO_2$ group.

This group will be designated in the following by G1bis.

A preferred group of medicaments according to the invention is constituted by those the active substance of which is a compound of formula (I) in which n is 1 and corresponds to the following formula (II):

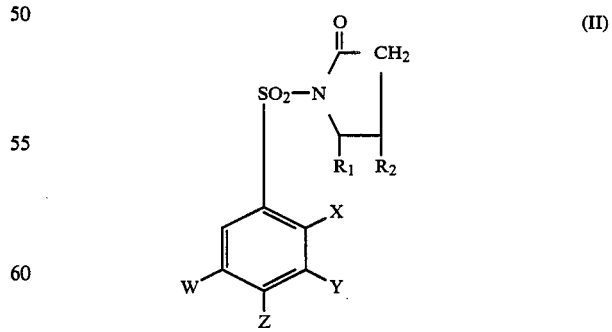

This group will be designated in the following by G2.

Another preferred group of medicaments according to the invention is constituted by those the active substance of which is a compound of formula (I) in which n is 2 and corresponds to the following formula (III):

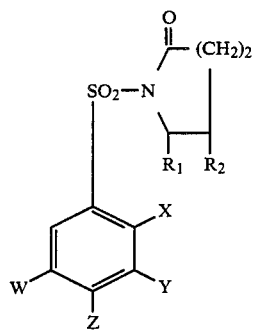 (III)

This group will be designated in the following by G3.

Another preferred group of medicaments according to the invention is constituted by those the active substance of which is a compound of formula (I) in which n is 3 and corresponds to the following formula (IV):

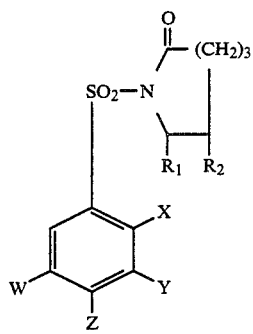 (IV)

This group will be designated in the following by G4.

Another preferred group of medicaments according to the invention is constituted by those the active substance of which is a compound of formula (I) in which $R_1$ represents H or $CH_3$.

This group will be designated in the following by G5.

Another preferred group of medicaments according to the invention is constituted by those the active substance of which is a compound of formula (I) in which $R_2$ represents H, OH or $OCOCH_3$.

This group will be designated in the following by G6.

Another preferred group of medicaments according to the invention is constituted by those the active substance of which is a compound of formula (I) in which Y represents $CF_3$, X represents H, and corresponding to the following formula (VII):

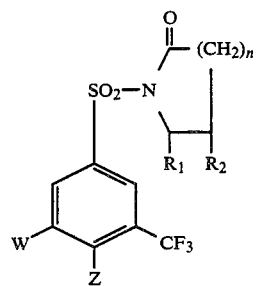 (VII)

and in which Z represents H or Cl and W represents H or $CF_3$.

This group will be designated in the following by G7.

Among group G7, a preferred group of medicaments according to the invention is constituted by those the active substance of which is a compound of formula (I) in which Z represents H and W represents $CF_3$ and corresponding to the following formula (VIII):

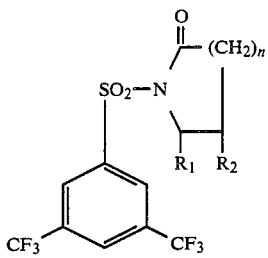 (VIII)

This group will be designated in the following by G8.

Among the group G7, another preferred group of medicaments according to the invention is constituted by those the active substance of which is a compound of formula (I) in which Z represents Cl and W represents H and corresponding to the following formula (IX):

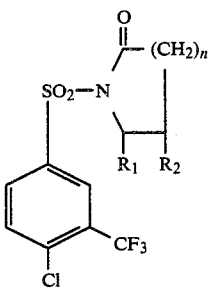 (IX)

This group will be designated in the following by G9.

Another preferred group of medicaments according to the invention is constituted by those the active substance of which is a compound of formula (I) in which X represents $OCH_3$, Y represents H and corresponding to the following formula (X):

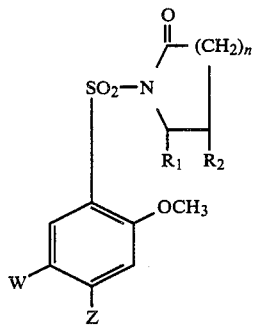 (X)

and in which Z represents H or $OCH_3$ and W represents H, Cl or $OCH_3$.

This group will be designated in the following by G10.

Among group G10, a preferred group of medicaments according to the invention is constituted by those the active substance of which is a compound of formula (I) in which Z represents H and W represents Cl and corresponding to the following formula (XI):

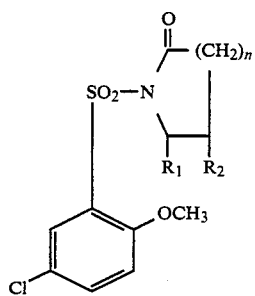

This group will be designated in the following by G11.

Among group G10, a preferred group of medicaments according to the invention is constituted by those the active substance of which of formula (I) in which Z represents OCH₃ and W represents H and corresponding to the following formula (XII):

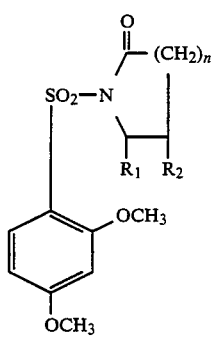

This group will be designated in the following by G12.

Among group G10, a preferred group of medicaments according to the invention is constituted by those the active substance of which is a compound of formula (I) in which Z represents OCH₃ and W represents OCH₃ and corresponding to the following formula (XIII):

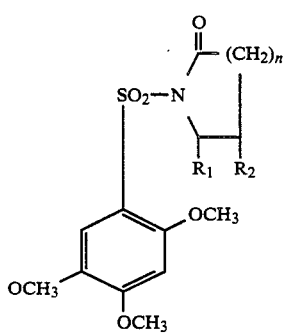

This group will be designated in the following by G13.

Among group G10, another preferred group of medicaments according to the invention is constituted by those the active substance of which is a compound of formula (I) in which Z represents OCH₃ and W represents Cl and corresponding to the corresponding formula (XIV):

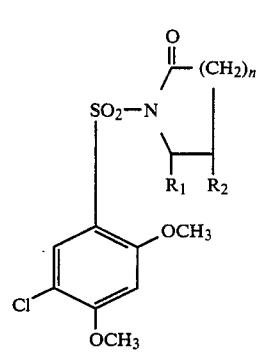

This group will be designated in the following by G14.

Another preferred group of medicaments according to the invention is constituted by those the active substance of which is a compound of formula (I) in which X represents H, Y represents H, Z represents OCH₃ and W represents H and corresponding to the following formula (XV):

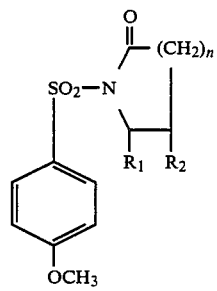

This group will be designated in the following by G15.

Another preferred group of medicaments according to the invention is constituted by those the active substance of which is a compound of formula (I) in which Y represents NO₂ and corresponding to the following formula (XVI):

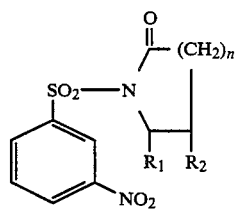

This group will be designated in the following by G16.

A preferred group of medicaments according to the invention is constituted by those the active substance of which is a compound of formula:

| Compound structure | Compounds n° |
|---|---|
| 2,4,5-trimethoxyphenyl-SO₂-N(propyl)-C(O)-CH₂- | 1 309 |
| 3-(CF₃)phenyl-SO₂-N(propyl)-C(O)-CH₂- | 1 043 |
| 3-(CF₃)phenyl-SO₂-N(CH(CH₃)CH₂-)-C(O)-CH₂- | 1 276 |
| 3-(CF₃)phenyl-SO₂-N(propyl)-C(O)-(CH₂)₃- | 1 277 |
| 4-Cl-2,5-dimethoxyphenyl-SO₂-N(CH(CH₃)CH₂-)-C(O)-CH₂- | 1 281 |

-continued

| Compound structure | Compounds n° |
|---|---|
| 4-methoxyphenyl-SO₂-N(propyl)-C(O)-CH₂- | 1 120 |
| 4-methoxyphenyl-SO₂-N(CH(CH₃)CH₂-)-C(O)-CH₂- | 1 288 |
| 4-Cl-3-(CF₃)phenyl-SO₂-N(CH₂CH(OH)CH₂-)-C(O)-CH₂- | 1 417 |
| 3,5-bis(CF₃)phenyl-SO₂-N(CH₂CH(OH)CH₂-)-C(O)-CH₂- | 1 418 |
| 3-(CF₃)phenyl-SO₂-N(CH₂CH(OH)CH₂-)-C(O)-CH₂- | 1 419 |

| | Compounds n° |
|---|---|
| 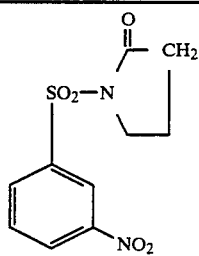 | 1 039 |

The compounds which are the active substance of the medicaments according to the invention and which are new correspond to the general formula (I):

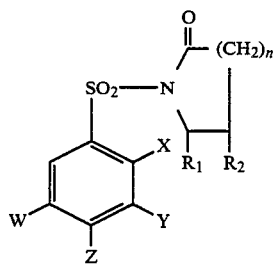  (I)

in which:
X represents a hydrogen atom, an alkoxy group from 1 to 4 carbon atoms;
Y represents a hydrogen atom, a $CF_3$ group, a $NO_2$ group;
Z represents a hydrogen atom, halogen, an alkoxy group from 1 to 4 carbon atoms, a $NO_2$ group;
W represents a hydrogen atom, halogen, a $CF_3$ group, a $NO_2$ group, an alkoxy group from 1 to 4 carbon atoms;
n is 1, 2 or 3;
$R_1$ represents a hydrogen atom, an alkyl group from 1 to 6 carbon atoms;
$R_2$ represents a hydrogen atom, an OH group, an OR group in which R represents an alkyl group from 1 to 4 carbon atoms or an acyl group from 1 to 6 carbon atoms; provided that when n is 1:
Y or W represents a $CF_3$ group; and when n is 2 or 3:
X or Z represents an alkoxy group from 1 to 4 carbon atoms or Y represents the $CF_3$ or $NO_2$ group.

The new industrial products according to the invention, which have just been defined, correspond to the G1bis group of medicaments above defined.

Preferred classes of compounds according to the invention are constituted by compounds corresponding to G1 to G9 groups above defined, in the framework of the medicaments and in which, when n is 1, Y or W represents $CF_3$, and when n is 2 or 3, either X or Z represents $OR_1$ or Y or W represents $CF_3$ or $NO_2$.

Another preferred class of compounds according to the invention is constituted by the compounds of formula (X) hereabove mentioned, in which n is 2 or 3, Z represents H or $OCH_3$, and W represents H, Cl or $OCH_3$.

Another preferred class of compounds according to the invention is constituted by compounds of formulae (XI), (XII), (XIII), (XIV), (XV), (XVI) above represented and in which n is 2 or 3.

A group of preferred compounds is constituted by those of formula:

| | Compounds n° |
|---|---|
| 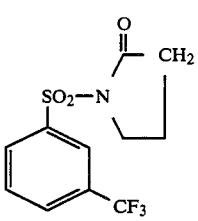 | 1 043 |
| 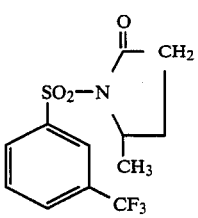 | 1 276 |
| 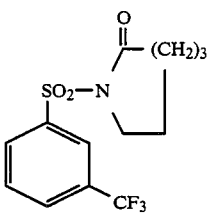 | 1 277 |
| 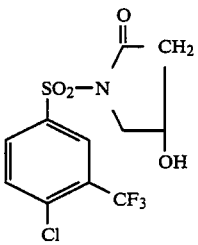 | 1 417 |
| 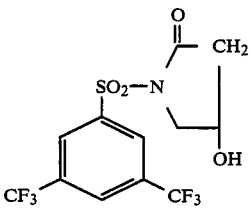 | 1 418 |
| 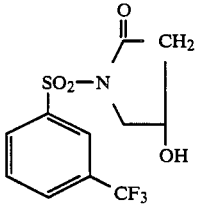 | 1 419 |

SYNTHESIS OF THE COMPOUNDS WHICH ARE THE ACTIVE SUBSTANCE OF MEDICAMENTS ACCORDING TO THE INVENTION AS WELL AS NEW COMPOUNDS ACCORDING TO THE INVENTION

The compounds of formula (I) may be obtained by cyclization of benzenesulfonamidoacid of formula (XVII):

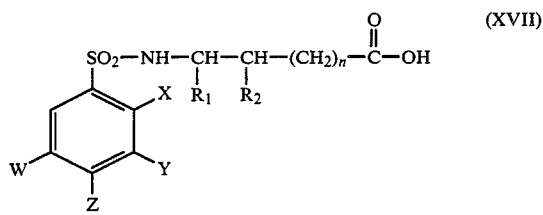

in which X, Y, Z, W, n, $R_1$ and $R_2$ have the previously indicated meanings.

Cyclization of benzenesulfonamides can be done by using a cyclizing agent, in an acid medium, and by heating. For example $P_2O_5$ can be used as a cyclizing agent and $H_3PO_4$ as an acid.

This method of preparing the compounds of formula (I) will be denoted by Method A.

The compounds according to the invention which can be prepared by this method A are those in which n is 1, $R_2$ represents hydrogen, and X, Y, Z and W are all different from an alkoxy group.

Below is given a general example of practising method A to obtain the compounds of formula (I).

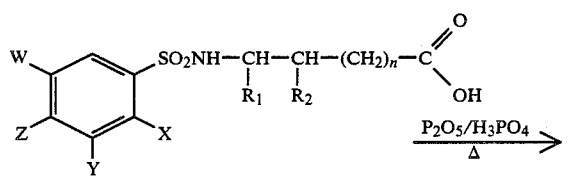

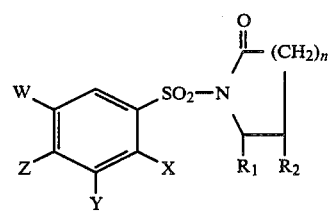

To 10 ml of 85% of orthophosphoric acid are added with care, 20 g of phosphoric anhydride and then 0.01 mole of a benzenesulfonamido-acid derivative. The reaction mixture is brought for 30 minutes to 3 hours to a temperature comprised between 40° and 90° C., according to the products, and then poured on cracked ice. The crystals are dried, washed abundantly with water, then with a N sodium bicarbonate solution.

The product is then recrystallized in the usual appropriate solvents.

The yield is from 60 to 90%.

The cyclizing of benzenesulfonamido-acids of formula (XVII) may also advantageously be effected by resorting to trifluoroacetic anhydride as cyclizing agent, in the presence of sodium trifluoroacetate and by heating it.

This method of production of compounds of formula (I) will be denoted in the following by Method B.

This method B has the advantage of being usuable for the preparation of any compounds of formula (I), and of providing a good yield.

Method B is preferably used when $R_2$ represents OH or $OCOCH_3$.

A general example of practising method B to obtain the compounds of formula (I) is given below:

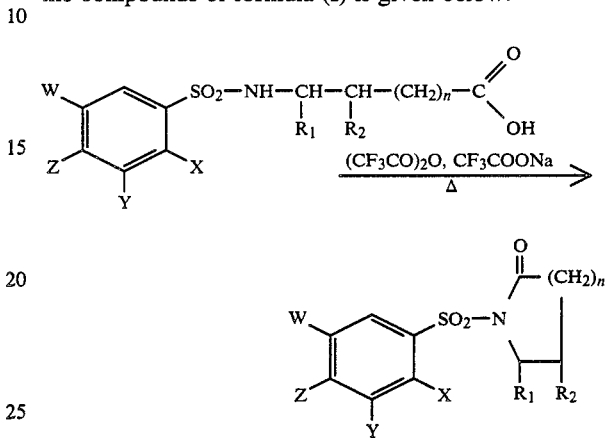

0.01 mole of benzenesulfonamido-acid derivative and 0.5 g of anhydrous sodium trifluoroacetate are brought to reflux with stirring in 20 ml of trifluoroacetic anhydride for 2 to 24 hours.

After evaporation of the reaction medium under vacuum, the residue is taken up again in 20 ml of anhydrous methanol and then brought to reflux for 30 minutes. The methanol solution is evaporated to dryness, and the residue is taken up in 10 ml of water.

The crystals are dried, then recrystallized in suitable organic solvents.

The yield is of from 65 to 90%.

The benzenesulfonamido-acids used are prepared as indicated in French patent application Nos. 81 11858 and 81 11859.

As regards the benzenesulfonamido-acids in which $R_2$ represents OH and n, $R_1$, X, Y, Z, W have the above indicated meanings, they are new.

These new benzenesulfonamido-acids correspond to the following formula (XVIIa):

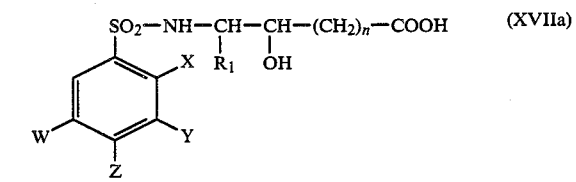

These compounds can be prepared by condensing a sulfohalogenide, particularly the sulfochloride of the formula (XVIII):

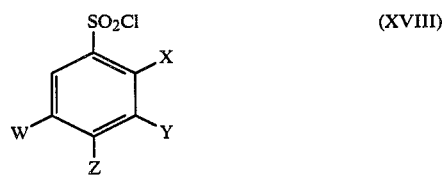

with an aminoacid of the formula:

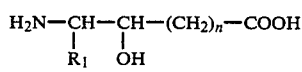

by methods such as described in French patent application Nos. 81 11858 and 81 11859.

The preparation of the compound of formula is given below by way of example:

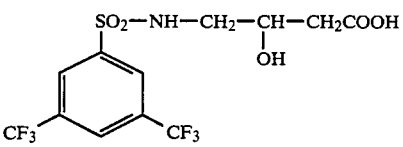

To 3.57 g (0.030 moles) of dl 4-amino-3-hydroxy butyric acid in 60 ml of N soda, is added drop by drop with vigourous stirring a solution of 9.4 g (0.030 moles) of 3,5-ditrifluoromethyl-benzenesulfonyl chloride in 60 ml of ethyl ether.

After 4 hours of stirring, the organic phase is removed. The aqueous phase is then brought to pH 3 with 2N hydrochloric acid. The precipitate formed is drained, washed with water until the disappearance of the chloride ions, then dried.

M. P.=160° C.; Yield=58%; m. w.=395.29.

Theoretical analysis for $C_{12}H_{11}F_6NO_5S$ Calculated: C 36.4; H 2.8; N 3.6; Found: C 36.3; H 3.1; N 3.8.

There are also prepared by this process, compounds of the formula:

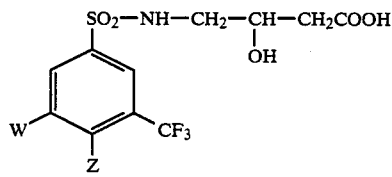

in which Z represents Cl and W represents H and Z represents H and W represents H.

The compounds of formula (I) according to the invention may also be prepared by condensation of sulfohalogenides, particularly sulfochlorides, of formula (XVIII):

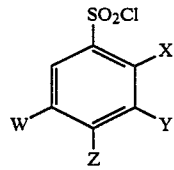     (XVIII)

in which X, Y, Z and W have the above indicated meanings with the compounds of the formula (XIX):

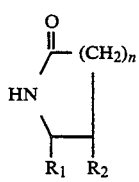     (XIX)

in which $R_1$, $R_2$ and n have the above indicated meanings.

This reaction is preferably carried out in the presence of a strong base, to take the proton from the compound (XIX), such as sodium hydride, in a solvent such as xylene and then under the effect of heating, condensation takes place.

This method will be denoted below by Method C.

The compounds according to the invention which can be prepared by this method are those in which $R_2$ represents hydrogen. Below is given a general example of the practising of method C.

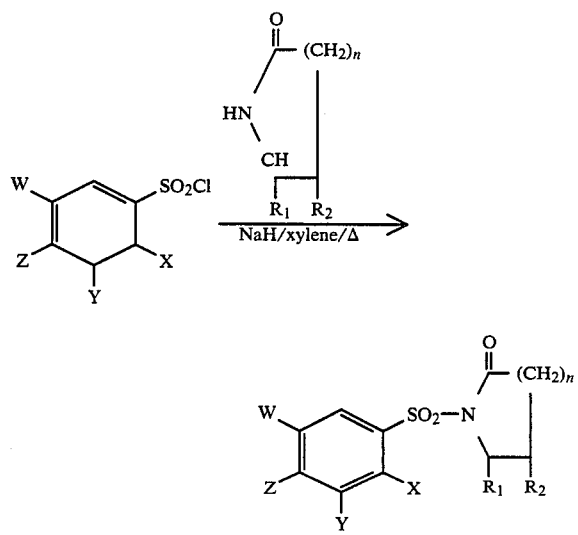

To 0.01 mole of sodium hydride in 50 ml of anhydrous xylene, is added drop by drop 0.01 mole of the lactam derivative, under stirring. The reaction medium is brought for 2 hours to 80° C. After cooling, 0.01 mole of the appropriate sulfochloride is added drop by drop and the reaction medium is brought to 110° C. for 2 to 8 hours.

After removal of the solvent by distillation under vacuum, the residue is taken up again in water. The precipitate is drained, washed with water, then recrystallized in the usual solvents.

The yield is from 10% to 50%.

The sulfochlorides used for practising method C are those described in the literature as well as in the patents and patent applications in France Nos. 2 313 918, 2 338 929, 2 504 528, 2 504 527.

The products which have been prepared by method A are the following ones: Nos. 1 043, 1 289, 1 277, 1 276, 1 355, 1 351, 1 416, 1 039.

The products which have been prepared by method B are the following ones: Nos. 1 043, 1 289, 1 277, 1 276, 1 355, 1 351, 1 416, 1 419, 1 417, 1 418, 1 415, 1 120, 1 287, 1 288, 1 124, 1 285, 1 286, 1 309, 1 332, 1 310, 1 281, 1 282, 1 442, 1 441, 1 039.

The products which have been prepared by method C are the following ones: Nos. 1 043, 1 289, 1 277, 1 276, 1 355, 1 351, 1 416, 1 120, 1 287, 1 288, 1 124, 1 285, 1 286, 1 309, 1 332, 1 310, 1 281, 1 442, 1 441.

The table below gathers the compounds prepared by methods A, B and C and indicates for each of them the formula, the melting point and the yield.

The percent analysis of the products obtained is in accordance with the usual standards (±0.3%).

GENERAL FORMULA

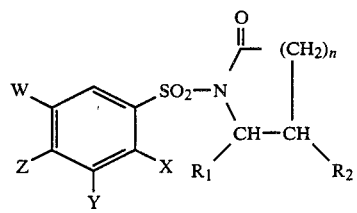

| Compound No. | X | Y | Z | W | n | $R_1$ | $R_2$ | Empirical formula | M.W. | M.P. °C. | Yield |
|---|---|---|---|---|---|---|---|---|---|---|---|
| 1043 | H | CF$_3$ | H | H | 1 | H | H | C$_{11}$H$_{10}$F$_3$NO$_3$S | 293.27 | 74 | 85 |
| 1289 | H | CF$_3$ | H | H | 2 | H | H | C$_{12}$H$_{12}$F$_3$NO$_3$S | 307.30 | 68 | 75 |
| 1277 | H | CF$_3$ | H | H | 3 | H | H | C$_{13}$H$_{14}$F$_3$NO$_3$S | 321.33 | 78 | 40 |
| 1276 | H | CF$_3$ | H | H | 1 | CH$_3$ | H | C$_{12}$H$_{12}$F$_3$NO$_3$S | 307.30 | 103 | 35 |
| 1355 | H | CF$_3$ | Cl | H | 1 | H | H | C$_{11}$H$_9$ClF$_3$NO$_3$S | 327.72 | 118 | 91 |
| 1351 | H | CF$_3$ | H | CF$_3$ | 1 | H | H | C$_{12}$H$_9$F$_6$NO$_3$S | 361.26 | 121 | 76 |
| 1416 | H | CF$_3$ | H | CF$_3$ | 2 | H | H | C$_{13}$H$_{11}$F$_6$NO$_3$S | 375.30 | 140 | 86 |
| 1419 | H | CF$_3$ | H | H | 1 | H | OH | C$_{11}$H$_{10}$F$_3$NO$_4$S | 309.27 | 100 | 64 |
| 1417 | H | CF$_3$ | Cl | H | 1 | H | OH | C$_{11}$H$_9$ClF$_3$NO$_4$S | 343.72 | 126 | 70 |
| 1418 | H | CF$_3$ | H | CF$_3$ | 1 | H | OH | C$_{12}$H$_9$F$_6$NO$_4$S | 377.26 | 120 | 66 |
| 1415 | H | CF | H | CF$_3$ | 1 | H | OCOCH$_3$ | C$_{14}$H$_{11}$F$_6$NO$_5$S | 419.31 | 105 | 75 |
| 1120 | H | H | OCH$_3$ | H | 1 | H | H | C$_{11}$H$_{13}$NO$_4$S | 255.30 | 134 | 75 |
| 1287 | H | H | OCH$_3$ | H | 2 | H | H | C$_{12}$H$_{15}$NO$_4$S | 269.32 | 105 | 60 |
| 1288 | H | H | OCH$_3$ | H | 1 | CH$_3$ | H | C$_{12}$H$_{15}$NO$_4$S | 269.32 | 113 | 45 |
| 1124 | OCH$_3$ | H | H | Cl | 1 | H | H | C$_{11}$H$_{12}$ClNO$_4$S | 289.75 | 148 | 50 |
| 1285 | OCH$_3$ | H | H | Cl | 1 | CH$_3$ | H | C$_{12}$H$_{14}$ClNO$_4$S | 303.77 | 126 | 45 |
| 1286 | OCH$_3$ | H | H | Cl | 3 | H | H | C$_{13}$H$_{16}$ClNO$_4$S | 317.80 | 160 | 30 |
| 1309 | OCH$_3$ | H | OCH$_3$ | OCH$_3$ | 1 | H | H | C$_{13}$H$_{17}$NO$_6$S | 315.35 | 168 | 45 |
| 1332 | OCH$_3$ | H | OCH$_3$ | OCH$_3$ | 1 | CH$_3$ | H | C$_{14}$H$_{19}$NO$_6$S | 329.38 | 147 | 40 |
| 1310 | OCH$_3$ | H | OCH$_3$ | Cl | 1 | H | H | C$_{12}$H$_{14}$ClNO$_5$S | 319.77 | 173 | 60 |
| 1281 | OCH$_3$ | H | OCH$_3$ | Cl | 1 | CH$_3$ | H | C$_{13}$H$_{16}$ClNO$_5$S | 333.80 | 152 | 55 |
| 1282 | OCH$_3$ | H | OCH$_3$ | Cl | 3 | H | H | C$_{14}$H$_{18}$ClNO$_5$S | 347.83 | 160 | 60 |
| 1458 | OCH$_3$ | H | OCH$_3$ | H | 1 | CH$_3$ | H | C$_{13}$H$_{17}$NO$_5$S | 299.35 | 151 | 45 |
| 1459 | OCH$_3$ | H | OCH$_3$ | H | 1 | H | H | C$_{12}$H$_{15}$NO$_5$S | 285.32 | 137 | 40 |
| 1039 | H | NO$_2$ | H | H | 1 | H | H | C$_{10}$H$_{10}$N$_2$O$_5$S | 270.27 | 173 | 85 |

The compounds according to the invention have remarkable pharmacological properties.

The compounds according to the invention have psychotropic properties with modifications of the behaviour.

These pharmacological properties have been studied by taking aniracetam as a reference substance.

The compounds according to the invention are advantageously introduced as active substance, particularly in the treatment of disorders of the memory, of amnesia, in the case of physical and intellectual efforts associated with periods of overactivity, in the treatment of disorders of behaviour and of adaptation.

The compounds according to the invention are distinguished by the fact that they act on the memory and the attention, increasing the mental activity and equilibrating emotional behaviour.

The compounds according to the invention are conditioned for this purpose with the traditional excipients and adjuvants, particularly those used for the preparation of tablets, powders, capsules, drinkable ampullae, drinkable solutions, injectable solutions.

The administration of medicaments containing the compounds according to the invention is effected preferably by the oral route, and the doses of compounds administered are comprised from 50 to 3 000 mg/day, preferably from 200 to 2 000 mg/day, for example 100 to 1 000 mg/day, in one or several doses.

An example of advantageous pharmaceutical composition is constituted by a tablet or a capsule corresponding to unit dosage of 25 to 200 mg of active substance, preferably 100 mg, in association with a pharmaceutically acceptable carrier.

Another example of advantageous pharmaceutical composition is constituted by a drinkable solution suitable with unit dosage of 25 to 200 mg of active substance.

I STUDY RELATING TO THE TOXICITY

The compounds according to the invention are devoid of toxicity.

In fact, the value of the LD$_{50}$ obtained with compounds Nos. 1 039, 1 043, 1 276, 1 288, administered intraperitoneally in the mouse, is higher than 1 g/kg, which shows that at the doses administered, the compounds of the invention are not toxic.

II STUDY OF THE CENTRAL NERVOUS SYSTEM

One resorts to a device constituted by a twopart cage, formed from a lit compartment and a dark compartment, separated by a partition pierced by a passage. The floor of the dark sector is formed by an electricifiable grid.

After familiarization with the device, albino mice underwent one by one the initiation session: each mouse was placed in the lit cmpartment; its spontaneous latency to enter the dark compartment (preferred spontaneously) was measured; as soon as it had entered, it received an electric shock.

After 10 minutes (protocol A), the animal was replaced in the lit compartment.

The effect is evaluated by the increase of the latency to enter the dark compartment, or the time passed in the same sector and study of its behaviour in each sector.

The products were administered intraperitoneously at 50 mg/kg in 2% of arabic gum, 20 minutes prior (procotol A) to the initiation session.

The placebo was constituted by 2% arabic gum.

The results relating to protocol A are given in table 2.

TABLE 2

| | | PROTOCOL A | |
|---|---|---|---|
| | Number of animals | Latency to enter the dark compartment at the initiation session | Times spent in the dark compartment during the 3 mn of the retention session |
| PLACEBO | 17 | 29,1 ± 6,1 | 20,3 ± 7,9 |
| No 1039 | 16 | 40,9 ± 8,6 | 38,7 ± 7,9 |
| No 1048 | 19 | 54,6 ± 8,4 | 30,3 ± 9,5 |
| No 1120 | 17 | 34,5 ± 5,9 | 24,5 ± 9,8 |
| No 1351 | 18 | 59,6 ± 12,2 | 30,1 ± 9,2 |
| No 1355 | 18 | 45,11 ± 7,8 | 33,9 ± 9,3 |
| ANIRACE-TAM | 16 | 45,2 ± 9,2 | 22,8 ± 9,4 |

The study of the behaviour of the mice shows that their exploratory capacity is increased in the two sectors, which is manifested by an increase in the latency of entry into the dark sector and an increase of the time passed in the dark sector.

III STUDY OF MOTOR ACTIVITY BY MEANS OF THE TEST CALLED "OPEN FIELD TEST"

This relates to a test recommended by JANSSEN et al. ("Psychopharmacologia", 1960, 1, p. 389-392) improved for the measurement of motor activity by an automatic apparatus by DELBENE et al. ("Psychologia", 1970, 18, p. 227-230).

This test has been adapted by G. NARCISSE et al. (unpublished work).

The doses were 50 and 100 mg/kg intraperitoneally.

This test carried out with compound No. 1 039 shows that this compound has psychotropic properties. This test, carried out under the same conditions with the compounds of the invention No. 1 403, 1 276, 1 277, 1 281, 1 288, 1 309, 1 417, 1 418 and 1 419, shows that these compounds also have a psychotropic activity.

We claim:

1. A compound of the formula

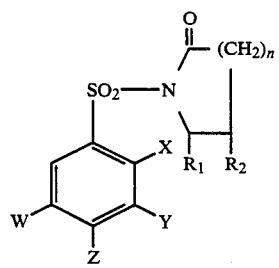

wherein:
X is selected from the group consisting of a hydrogen atom and an alkoxy group having from 1 to 4 carbon atoms;
Y is selected from the group consisting of a hydrogen atom, a $CF_3$ group, and a $NO_2$ group;
Z is selected from the group consisting of a hydrogen atom, halogen, an alkoxy group having from 1 to 4 carbon atoms and a $NO_2$ group;
W is selected from the group consisting of a hydrogen atom, halogen, a $CF_3$ group, a $NO_2$ group, and an alkoxy group having from 1 to 4 carbon atoms;
n is 1,2 or 3;
$R_1$ is selected from the group consisting of a hydrogen atom, and an aklyl group having from 1 to 6 carbon atoms;
$R_2$ is selected from the group consisting of a hydrogen atom, an OH group, an OR group wherein R is selected from the group consisting of an aklyl group having from 1 to 4 carbon atoms or a carboxylic acyl group having from 1 to 6 carbon atoms;
provided that when n is 1:
Y or W is a $CF_3$ group; and when n is 2 or 3:
X or Z is an alkoxy group having from 1 to 4 carbon atoms or Y or W is a $CF_3$ or $NO_2$ group.

2. A compound of claim 1, wherein $R_1$ is selected from the group consisting of H and $CH_3$.

3. A compound of claim 1 wherein R is selected from the group consisting of H, OH and $OCOCH_3$.

4. A compound of claim 1 of the formula:

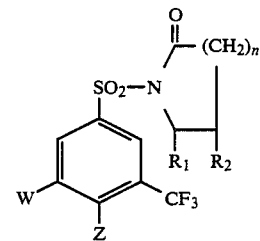

wherein n, $R_1$, $R_2$ have the meanings indicated in claim 1, Z is selected from the group consisting of H and Cl and W is selected from the group consisting of H and $CF_3$.

5. A compound of claim 1 of the formula:

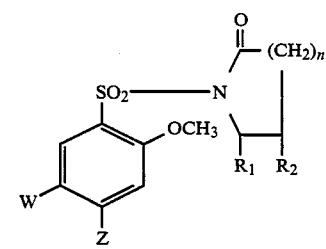

wherein n is 2 or 3, $R_1$ and $R_2$ have the meanings indicated in claim 1, Z is selected from the group consisting of H and $OCH_3$ and W is selected from the group consisting of H, Cl and $OCH_3$.

6. A compound of claim of the formula:

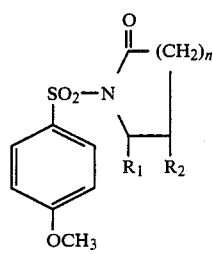

wherein n is 2 or 3, $R_1$ and $R_2$ have the meanings indicated in claim 1.

7. A compound of claim 1 of the formula

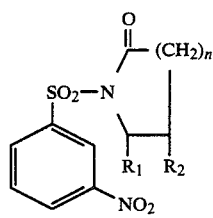

wherein n is 2 or 3, $R_1$ and $R_2$ have the meanings indicated in claim 1.

8. A compound of claim 1, having a formula selected from the group consisting of:

| | Compound no |
|---|---|
| (structure) | 1 043 |
| (structure) | 1 276 |
| (structure) | 1 277 |
| (structure) | 1 417 |
| (structure) | 1 418 |
| (structure) | 1 419 |

9. A psychotopic composition which comprises a pharmaceutically acceptable carrier and in a therapeutically effective amount a compound of the formula:

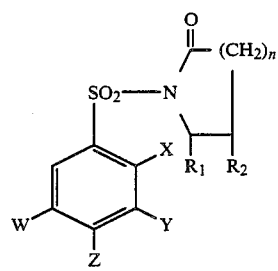

wherein:
X is selected from the group consisting of a hydrogen atom, and an alkoxy group having from 1 to 4 carbon atoms;
Y is selected from the group consisting of a hydrogen atom, a $CF_3$ group, and a $NO_2$ group;
Z is selected from the group consisting of a hydrogen atom, halogen, an alkoxy group having from 1 to 4 carbon atoms, and a $NO_2$ group;
W is selected from the group consisting of a hydrogen atom, halogen, a $CF_3$ group, a $NO_2$ group, and an alkoxy group having from 1 to 4 carbon atoms;
n is 1, 2 and 3;
$R_1$ is selected from the group consisting of a hydrogen atom, and an alkyl group having from 1 to 6 carbon atoms;
$R_2$ is selected from the group consisting of a hydrogen atom, an OH group, an OR group in which R is selected from the group consisting of an alkyl group having from 1 to 4 carbon atoms and a carboxylic acyl group having from 1 to 6 carbon atoms provided that X or Z is an alkoxy group having from 1 to 4 carbon atoms or Y or W is selected from the group consisting of $CF_3$ and $NO_2$.

10. The composition of claim 9 wherein the compound has the formula:

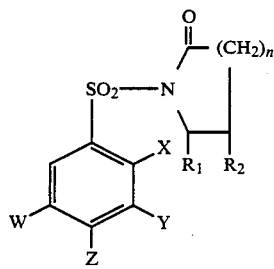

wherein:
X is selected from the group consisting of a hydrogen atom and an alkoxy group having from 1 to 4 carbon atoms;
Y is selected from the group consisting of a hydrogen atom, a $CF_3$ group, and a $NO_2$ group;
Z is selected from the group consisting of a hydrogen atom, halogen, an alkoxy group having from 1 to 4 carbon atoms, and a $NO_2$ group;
W is selected from the group consisting of a hydrogen atom, halogen, a $CF_3$ group, a $NO_2$ group, and an alkoxy group having from 1 to 4 carbon atoms;
n is 1, 2 or 3:
$R_1$ is selected from the group consisting of a hydrogen atom, and an alkyl group having from 1 to 6 carbon atoms;
$R_2$ is selected from the group consisting of a hydrogen atom, an OH group, and an OR group in which R represents an alkyl group having from 1 to 4 carbon atoms or a carboxylic acyl group having from 1 to 6 carbon atoms;
provided that when n is 1:
Y or W is $CF_3$, and when n is 2 or 3:
X or Z is selected from the group consisting of an alkoxy group having from 1 to 4 carbon atoms or Y or W is selected from the group of the $CF_3$ and $NO_2$.

11. The composition of claim 9 or 10 wherein $R_1$ is selected from the group consisting of hydrogen and $CH_3°$.

12. The composition of claim 9 or 10 wherein $R_2$ is selected from the group consisting of hydrogen, hydroxy and $OCOCH_3$.

13. The composition of claim 9 wherein the compound has the formula

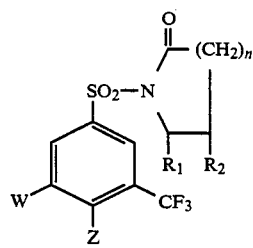

wherein
$R_1$ is selected from the group consisting of hydrogen and an alkyl group having from 1 to 6 carbons,
$R_2$ is selected from the group consisting of hydrogen, hydroxy, and OR in wich R is an alkyl from group having 1 to 4 carbons, an acyl group having from 1 to 6 carbons
n is selected from the group consisting of 1, 2 and 3;
W is selected from the group consisting of hydrogen and $CF_3°$, and
Z is selected from the group consisting of hydrogen and Cl.

14. The composition of claim 9 wherein the compound has the formula

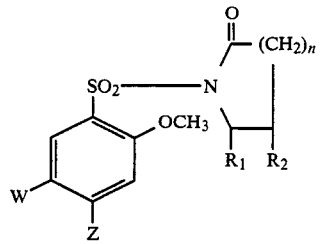

wherein
$R_1$ is selected from the group consisting of hydrogen and an alkyl group having from 1 to 6 carbons,
$R_2$ is selected from the group consisting of hydrogen, hydroxy, and OR in which R is selected from the group consisting of an alkyl group having from 1 to 4 carbons and a carboxylic acyl group having from 1 to 6 carbons
n is selected from the group consisting of 1, 2 and 3;
Z is selected from the group consisting of hydrogen and $OCH_3$; and
W is selected from the group consisting of hydrogen, Cl and $OCH_3$.

15. The composition of claim 9 wherein the compound has the formula

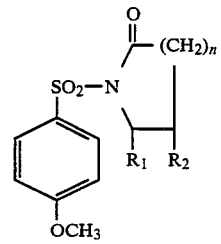

wherein $R_1$ is selected from the group consisting of hydrogen and an alkyl group having from 1 to 6 carbons; $R_2$ is hydrogen, hydroxy, and OR in which R is selected from the group consisting of an alkyl group having from 1 to 4 carbons, and a carboxylic acyl group having from 1 to 6 carbons; and n is selected from the group consisting of 1, 2 and 3.

16. The composition of claim 9 wherein the compound has the formula

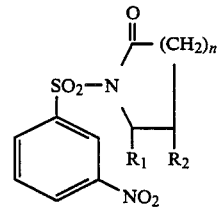

wherein $R_1$ is selected from the group consisting of hydrogen and an alkyl group having 1 to 6 carbons;
$R_2$ is selected from the group consisting of hydrogen, hydroxy, OR in which R is selected from the group consisting of an alkyl group having from 1 to 4 carbons and a carboxylic acyl group having from 1 to 6 carbons; and n is selected from the group consisting of 1, 2 and 3.

17. The composition of claim 9 which is suitable for oral administration.

18. The composition of claim 9 wherein unit dosage contains from 25 to 250 mg of active compound.

19. A method for effecting a psychotropic effect in a host which comprises administering to said host a pharmaceutically acceptable carrier and a psychotropically effective amount, the compound of claim 1.

* * * * *